United States Patent
Ricci et al.

(10) Patent No.: US 10,835,369 B2
(45) Date of Patent: *Nov. 17, 2020

(54) SOFT-TISSUE FIXATION DEVICE

(71) Applicant: Cable Fix LLC, Hernando, MS (US)

(72) Inventors: William Ricci, Richmond Heights, MO (US); Mark Brinker, Houston, TX (US); Carey Bryant, Hernando, MS (US)

(73) Assignee: CABLE FIX LLC, Hernando, MS (US)

( * ) Notice: Subject to any disclaimer, the term of this patent is extended or adjusted under 35 U.S.C. 154(b) by 277 days.

This patent is subject to a terminal disclaimer.

(21) Appl. No.: 15/900,504

(22) Filed: Feb. 20, 2018

(65) Prior Publication Data
US 2018/0168798 A1    Jun. 21, 2018

Related U.S. Application Data

(63) Continuation of application No. 14/961,496, filed on Dec. 7, 2015, now Pat. No. 10,022,216.

(51) Int. Cl.
*A61F 2/08* (2006.01)
*A61B 17/08* (2006.01)
(Continued)

(52) U.S. Cl.
CPC ........ *A61F 2/0811* (2013.01); *A61B 17/0643* (2013.01); *A61B 17/08* (2013.01); *A61B 17/1146* (2013.01); *A61B 2017/0464* (2013.01); *A61B 2017/0641* (2013.01); *A61B 2090/064* (2016.02); *A61F 2002/0829* (2013.01); *A61F 2002/0864* (2013.01); *A61F 2002/0888* (2013.01); *Y10T 24/463* (2015.01)

(58) Field of Classification Search
CPC ... A61B 17/064; A61B 17/0643; A61B 17/08; A61B 2017/0412; A61B 2017/0454; A61B 2017/0464; A61B 2017/0641; A61B 2017/0646; A61B 2017/081; A61F 2/0811; A61F 2002/0817; A61F 2002/0823; A61F 2002/0829; A61F 2002/0847; A61F 2002/0864; A61F 2002/087; A61F 2002/0888; Y10T 24/34; Y10T 24/3499; Y10T 24/44077; Y10T 24/45; Y10T 24/45225; Y10T 24/463
See application file for complete search history.

(56) References Cited

U.S. PATENT DOCUMENTS

| 479,938 | A | * | 8/1892 | Fredlihp | ......... | A44B 9/12 |
| | | | | | | 24/707.7 |
| 899,612 | A | * | 9/1908 | Phillips | ......... | B65D 33/1675 |
| | | | | | | 24/30.5 R |

(Continued)

OTHER PUBLICATIONS

Notice of Allowance for U.S. Appl. No. 14/961,496 dated Mar. 28, 2018.

*Primary Examiner* — Ryan J. Severson
(74) *Attorney, Agent, or Firm* — Kunzler Bean & Adamson

(57) ABSTRACT

A system for fixating soft-tissue is described herein. The system includes a soft-tissue fixation device comprising a cable-retention feature. Additionally, the system includes a cable coupleable to the cable-retention feature of the soft-tissue fixation device. The cable is configured to be tensioned to a measurable and adjustable tension.

13 Claims, 6 Drawing Sheets

(51) Int. Cl.
*A61B 17/064* (2006.01)
*A61B 17/11* (2006.01)
*A61B 17/04* (2006.01)
*A61B 90/00* (2016.01)

(56) References Cited

U.S. PATENT DOCUMENTS

| | | | | |
|---|---|---|---|---|
| 3,166,072 A * | 1/1965 | Sullivan, Jr. | A61B 17/1114 | 606/153 |
| 4,060,089 A * | 11/1977 | Noiles | A61B 17/0643 | 606/220 |
| 4,532,927 A * | 8/1985 | Miksza, Jr. | A61B 17/0643 | 606/220 |
| 4,534,350 A * | 8/1985 | Golden | A61B 17/0643 | 606/220 |
| 4,534,352 A * | 8/1985 | Korthoff | A61B 17/0643 | 606/220 |
| 4,548,202 A * | 10/1985 | Duncan | A61B 17/0643 | 606/220 |
| 4,573,469 A * | 3/1986 | Golden | A61B 17/068 | 411/363 |
| 4,610,250 A * | 9/1986 | Green | A61B 17/0643 | 411/450 |
| 4,754,758 A * | 7/1988 | Li | A61B 17/04 | 606/213 |
| 4,932,960 A * | 6/1990 | Green | A61B 17/0643 | 606/220 |
| 5,358,510 A * | 10/1994 | Luscombe | A61B 17/0643 | 606/151 |
| 5,478,353 A * | 12/1995 | Yoon | A61B 17/0057 | 606/104 |
| 5,620,452 A * | 4/1997 | Yoon | A61B 17/0643 | 606/151 |
| 5,665,109 A * | 9/1997 | Yoon | A61B 17/0469 | 606/139 |
| 5,797,932 A * | 8/1998 | Min | A61B 17/0401 | 606/151 |
| 6,276,032 B1 * | 8/2001 | Nortman | A44B 18/0065 | 24/572.1 |
| 6,685,708 B2 * | 2/2004 | Monassevitch | A61B 17/0642 | 606/324 |
| 6,712,830 B2 * | 3/2004 | Esplin | A61B 17/0401 | 606/152 |
| 6,966,919 B2 * | 11/2005 | Sixto, Jr. | A61B 17/0643 | 606/139 |
| 7,033,378 B2 * | 4/2006 | Smith | A61B 17/0643 | 606/151 |
| 7,094,251 B2 * | 8/2006 | Bonutti | A61B 17/0487 | 606/232 |
| 7,678,122 B2 * | 3/2010 | Kortenbach | A61B 17/0643 | 606/139 |
| 7,854,750 B2 * | 12/2010 | Bonutti | A61B 17/0487 | 606/232 |
| 7,985,241 B2 * | 7/2011 | Smith | A61B 17/0643 | 606/151 |
| 8,080,020 B2 * | 12/2011 | Kortenbach | A61B 17/0643 | 606/139 |
| 8,114,100 B2 * | 2/2012 | Smith | A61B 17/00234 | 24/706.4 |
| 8,162,977 B2 * | 4/2012 | Bonutti | A61B 17/0487 | 606/232 |
| 8,454,628 B2 * | 6/2013 | Smith | A61B 17/0643 | 606/139 |
| 8,613,750 B2 * | 12/2013 | Smith | A61B 17/0643 | 606/151 |
| 9,039,596 B2 * | 5/2015 | Sater | A61B 17/0401 | 600/29 |
| 9,220,503 B2 * | 12/2015 | Ranchod | A61B 17/083 | |
| 9,788,827 B2 * | 10/2017 | Miksza | A61B 17/282 | |
| 10,022,216 B2 * | 7/2018 | Ricci | A61B 17/0643 | |
| 10,231,769 B2 * | 3/2019 | Ricci | A61B 17/8861 | |
| 10,327,825 B2 * | 6/2019 | Brinker | A61B 17/8883 | |
| 10,349,996 B2 * | 7/2019 | Bryant | A61B 17/8863 | |
| 10,433,891 B2 * | 10/2019 | Brinker | A61B 17/862 | |
| 2001/0051815 A1 * | 12/2001 | Esplin | A61B 17/0401 | 606/232 |
| 2002/0029044 A1 * | 3/2002 | Monassevitch | A61B 17/0642 | 606/75 |
| 2004/0044366 A1 * | 3/2004 | Bonutti | A61B 17/0487 | 606/232 |
| 2004/0059349 A1 * | 3/2004 | Sixto, Jr. | A61B 17/0643 | 606/139 |
| 2004/0059354 A1 * | 3/2004 | Smith | A61B 17/0643 | 606/151 |
| 2004/0059358 A1 * | 3/2004 | Kortenbach | A61B 17/0643 | 606/153 |
| 2007/0032825 A1 * | 2/2007 | Bonutti | A61B 17/0487 | 606/232 |
| 2008/0046007 A1 * | 2/2008 | Schwemberger | A61B 17/0643 | 606/220 |
| 2008/0046008 A1 * | 2/2008 | Smith | A61B 17/0643 | 606/220 |
| 2008/0108897 A1 * | 5/2008 | Bonutti | A61B 17/0487 | 600/439 |
| 2008/0140095 A1 * | 6/2008 | Smith | A61B 17/00234 | 606/151 |
| 2008/0147116 A1 * | 6/2008 | Smith | A61B 17/0643 | 606/220 |
| 2008/0149685 A1 * | 6/2008 | Smith | A61B 17/0643 | 227/181.1 |
| 2010/0179568 A1 * | 7/2010 | Kortenbach | A61B 17/0643 | 606/139 |
| 2011/0040307 A1 * | 2/2011 | Ranchod | A61B 17/083 | 606/142 |
| 2011/0092993 A1 * | 4/2011 | Jacobs | A61B 17/0643 | 606/153 |
| 2011/0201877 A1 * | 8/2011 | Sater | A61B 17/0401 | 600/37 |
| 2012/0130374 A1 * | 5/2012 | Bouduban | A61B 17/0642 | 606/75 |
| 2012/0143247 A1 * | 6/2012 | Smith | A61B 17/0643 | 606/220 |
| 2016/0081686 A1 * | 3/2016 | Miksza | A61B 17/122 | 606/151 |
| 2016/0100835 A1 * | 4/2016 | Linder | A61B 17/0644 | 606/220 |
| 2016/0346023 A1 * | 12/2016 | Bouduban | A61B 17/0642 | |
| 2017/0156738 A1 * | 6/2017 | Ricci | A61B 17/8861 | |
| 2017/0156771 A1 * | 6/2017 | Brinker | A61B 17/8883 | |
| 2017/0156772 A1 * | 6/2017 | Brinker | A61B 17/8883 | |
| 2017/0156774 A1 * | 6/2017 | Bryant | A61B 17/8685 | |
| 2017/0156775 A1 * | 6/2017 | Bryant | A61B 17/8685 | |
| 2017/0156779 A1 * | 6/2017 | Bryant | A61B 17/8863 | |
| 2017/0156847 A1 * | 6/2017 | Ricci | A61F 2/0811 | |
| 2018/0168798 A1 * | 6/2018 | Ricci | A61F 2/0811 | |

\* cited by examiner

SOFT-TISSUE FIXATION DEVICE

CROSS-REFERENCE TO RELATED APPLICATION

This application is a continuation of U.S. patent application Ser. No. 14/961,496, filed Dec. 7, 2015, which is incorporated herein by reference.

FIELD

The subject matter of the present disclosure relates generally to soft-tissue fixation devices. More specifically, the present disclosure relates to repairing damaged or torn tendons, ligaments, and muscles using soft-tissue fixation devices and attaching the soft-tissue to bone.

BACKGROUND

Damaged or torn soft-tissues, such as tendons, ligaments, and muscles, can be difficult to repair. While traditional sutures may be used to repair damaged or torn soft-tissue, the repeated strain and tension experienced by tendons and other soft-tissues often cause the sutures to fail. Accordingly, traditional sutures usually require extensive reinforcement in order to be employed for repairing soft-tissue, especially when the sutures are used to reattach soft-tissue to bone. Conventional reinforcement configurations often increase the overall complexity of a surgical procedure and often result in extra incisions, drilling, and anchoring, thus potentially adversely affecting adjacent tissues and the patient's recovery time.

SUMMARY

From the foregoing discussion, it should be apparent that a need exists for an apparatus, system, and method for repairing soft-tissue that overcome the limitations of conventional medical tools and procedures. Beneficially, such an apparatus, system, and method would improve the ease, efficiency, and effectiveness of medical procedures that involve repairing soft-tissue and/or reattaching soft-tissue to bone.

The subject matter of the present application has been developed in response to the present state of the art, and in particular, in response to the problems and needs in the art that have not yet been fully solved by currently available medical tools and procedures. Accordingly, the present disclosure has been developed to provide a soft-tissue fixation device, and its related systems and methods, that overcome many or all of the above-discussed shortcomings in the art.

According to one embodiment, a system for fixating soft-tissue includes a soft-tissue fixation device comprising a cable-retention feature. The system also includes a cable coupleable to the cable-retention feature of the soft-tissue fixation device, wherein the cable is configured to be tensioned to a measurable and adjustable tension, to cause, in some implementations, compression of bone, compression of soft tissue to bone, and/or compression of soft tissue to other soft tissue with a measurable and adjustable compression.

Disclosed herein is one embodiment of a soft-tissue fixation device. The soft-tissue fixation device includes a first plate, a plurality of tines, and a second plate. The first plate has a first clamping surface and is configured to be positioned on a first side of a soft-tissue segment. The second plate has a second clamping surface and is configured to be positioned on a second side of a soft-tissue segment. The tines extend from the first clamping surface and may be substantially parallel to each other. The respective clamping surfaces of the first and second plate are configured to face each other and the tines are configured to extend through the soft-tissue segment. In such an embodiment, one of the first plate and the second plate has at least one spacing member and the other of the first plate and the second plate has at least one engagement feature configured to engage the at least one spacing member. Engagement between the at least one spacing member and the at least one engagement feature maintains a predetermined distance between the first clamping surface and the second clamping surface that is more than a length of any one of the tines.

According to one implementation, the tines extend substantially perpendicularly from the first clamping surface. In another implementation, the first plate has at least one cable hole extending perpendicular to the plurality of tines. In one implementation, the plurality of tines has peripheral tines and middle tines, the peripheral tines having tips of a first configuration and the middle tines having tips of a second configuration, the first configuration being different than the second configuration.

In one implementation, spacing between adjacent tines of the plurality of tines and the predetermined distance between the first clamping surface and the second clamping surface enable the soft-tissue fixation device to be securely attached to the soft-tissue segment while still allowing blood to circulate through the soft-tissue segment. In one implementation, each of the tines has a non-circular cross-section. In another implementation, each of the tines has the same length.

According to another implementation, the at least one spacing member has two prongs made from a resiliently flexible material with a gap interposed between the two prongs. In such a configuration, the prongs are bendable inwards toward each other. Each prong has a tip converging towards the gap in a direction from the first clamping surface to the second clamping surface and each prong has a notch on a lateral side. The at least one engagement feature has a hole having a lip. The two prongs are configured to bend inwards as the tip of each prong engages the lip of the hole upon insertion of the at least one spacing member into the hole until the lip is receivably engaged in the notch.

In one implementation, one or both of the first and second plates has one or more pass-through apertures extending through one or both of the first and second plates, respectively. In one implementation, the plurality of tines forms an array of tines, the at least one spacing member is two spacing members and the at least one engagement feature is two engagement features. In such a configuration, the array of tines is interposed between the two spacing members and the two engagement features. Accordingly, the array of tines has a width and the width is less than a distance between the two spacing members. In one implementation, the array of tines includes multiple rows of tines, wherein a distance between adjacent rows is about 0.075 inches. The clamping surface may be planar and the first plate may have an outer surface opposing the first clamping surface that is substantially contoured.

Also disclosed herein is another embodiment of a soft-tissue fixation device. The soft-tissue fixation device includes a plate having a first clamping surface and a plurality of tines extending from the first clamping surface. The plate is configured to be positioned on a first side of a soft-tissue and the plurality of tines are configured to extend through the soft-tissue. The plurality of tines are constructed from a shape-memory alloy, such that when the temperature of the plurality of tines raises or lowers to a predetermined temperature, the plurality of tines undergoes deformation/bending.

According to one implementation, the plurality of tines are substantially parallel to each other. Spacing between adjacent tines of the plurality of tines and torsional deformation contribute to the ability of the soft-tissue fixation device to securely attach to the soft-tissue segment while still allowing blood to circulate through the soft-tissue segment.

Also disclosed herein is one embodiment of a method for stapling soft-tissue. The method includes positioning a first plate on a first side of a soft-tissue segment. The first plate includes a first clamping surface and a plurality of tines extend from the first clamping surface. The method further includes positioning a second plate on a second side of the soft-tissue segment and extending the plurality of tines through the soft-tissue segment. After extending the plurality of tines through the soft-tissue segment, the method includes coupling the first plate to the second plate by engaging at least one spacing member of one of the first plate and the second plate with at least one engagement feature of the other of the first plate and the second plate. Engagement between the at least one spacing member and the at least one engagement feature maintains a predetermined distance between the first clamping surface and the second clamping surface that is more than a length of any one of the tines.

In one implementation, the soft-tissue segment is a first soft-tissue segment and positioning the first plate on the first side of the first soft-tissue segment further includes positioning the first plate on a first side of a second soft-tissue segment. In such an implementation, positioning the second plate on the second side of the first soft-tissue segment includes positioning the second plate on a second side of the second soft-tissue segment and extending the plurality of tines through the first soft-tissue segment includes extending a first grouping of the plurality of tines through only the first soft-tissue segment, extending a second grouping of the plurality of tines through only the second soft-tissue segment, and extending a third grouping of the plurality of tines through both the first and second soft-tissue segments to couple the first and second soft-tissue segments together. According to another implementation, the method further includes overlapping the first and second soft-tissue segments prior to extending the plurality of tines through the first and second soft-tissue segments.

According to another embodiment, a method for fixating soft-tissue includes fixedly securing a soft-tissue segment with a soft-tissue fixation device, connecting a cable to the soft-tissue fixation device, and tensioning the cable to a measurable and adjustable tension to fixate the soft-tissue fixation device, and the soft-tissue segment fixedly secured with the soft-tissue fixation device, relative to an object. In some implementations, the method further includes connecting the cable to bone such that tensioning the cable to a measurable and adjustable tension fixates the soft-tissue fixation device, and the soft-tissue segment fixedly secured with the soft-tissue fixation device, relative to the bone. In yet other implementations, the soft-tissue fixation device is a first soft-tissue fixation device, the soft-tissue segment is a first soft-tissue segment, and the method further includes fixedly securing a second soft-tissue segment with a second soft-tissue fixation device. In such implementations, the method can further include connecting the cable to the second soft-tissue fixation device such that tensioning the cable to a measurable and adjustable tension fixates the first soft-tissue fixation device, and the first soft-tissue segment fixedly secured with the first soft-tissue fixation device, relative to the second soft-tissue fixation device, and the second soft-tissue segment fixedly secured with the second soft-tissue fixation device.

According to one implementation of the method, tensioning the cable to a measurable and adjustable tension comprises compressing the soft-tissue segment, with a measurable and adjustable compression, against bone, another soft-tissue segment, or both.

Reference throughout this specification to features, advantages, or similar language does not imply that all of the features and advantages that may be realized with the present disclosure should be or are in any single embodiment of the disclosure. Rather, language referring to the features and advantages is understood to mean that a specific feature, advantage, or characteristic described in connection with an embodiment is included in at least one embodiment of the subject matter disclosed herein. Thus, discussion of the features and advantages, and similar language, throughout this specification may, but do not necessarily, refer to the same embodiment.

Furthermore, the described features, advantages, and characteristics of the disclosure may be combined in any suitable manner in one or more embodiments. One skilled in the relevant art will recognize that the subject matter of the present application may be practiced without one or more of the specific features or advantages of a particular embodiment. In other instances, additional features and advantages may be recognized in certain embodiments that may not be present in all embodiments of the disclosure. Further, in some instances, well-known structures, materials, or operations are not shown or described in detail to avoid obscuring aspects of the subject matter of the present disclosure. These features and advantages of the present disclosure will become more fully apparent from the following description and appended claims, or may be learned by the practice of the disclosure as set forth hereinafter.

BRIEF DESCRIPTION OF THE DRAWINGS

In order that the advantages of the disclosure will be readily understood, a more particular description of the disclosure briefly described above will be rendered by reference to specific embodiments that are illustrated in the appended drawings. Understanding that these drawings depict only typical embodiments of the disclosure and are not therefore to be considered to be limiting of its scope, the subject matter of the present application will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

In the following description, numerous specific details are provided. One skilled in the relevant art will recognize, however, that the subject matter of the present application may be practiced without one or more of the specific details, or with other methods, components, materials, and so forth. In other instances, well-known structures, materials, or operations are not shown or described in detail to avoid obscuring aspects of the disclosure. Also, like reference numbers (e.g., 120 and 220) refer to like components (e.g., different embodiments of the same component).

Illustrated in FIGS. 1A-4 are several representative embodiments of a soft-tissue fixation device for repairing damaged or torn soft-tissues, such as tendons and ligaments. In some implementations, the soft-tissue fixation device is configured to both fixate soft tissue relative to the soft-tissue fixation device and fixate the soft tissue relative to bone. More specifically, with the soft tissue fixated or secured by the soft-tissue fixation device, the soft-tissue fixation device can be fixated to bone by securing at least one tensionable cable to the soft-tissue fixation device and fixating the cable relative to the bone by tensioning the cables. Accordingly, the soft-tissue fixation device can be any device configured to fixate soft tissue, such as clamps, staples, braces, bands, clasps, and the like. In this regard, although the example of the soft-tissue fixation device specifically described and illustrated herein resembles a clamp, with two separate portions configured to fixate soft tissue between them, in other embodiments, the soft-tissue fixation device can be configured more like a staple, with a single portion that bends or deforms to fixate soft tissue. As described herein, the soft-tissue fixation device provides various advantages and benefits over other medical tools and procedures. However, the recited advantages are not meant to be limiting in any way, as one skilled in the art will appreciate that other advantages may also be realized upon practicing the present disclosure.

Figure 1A:
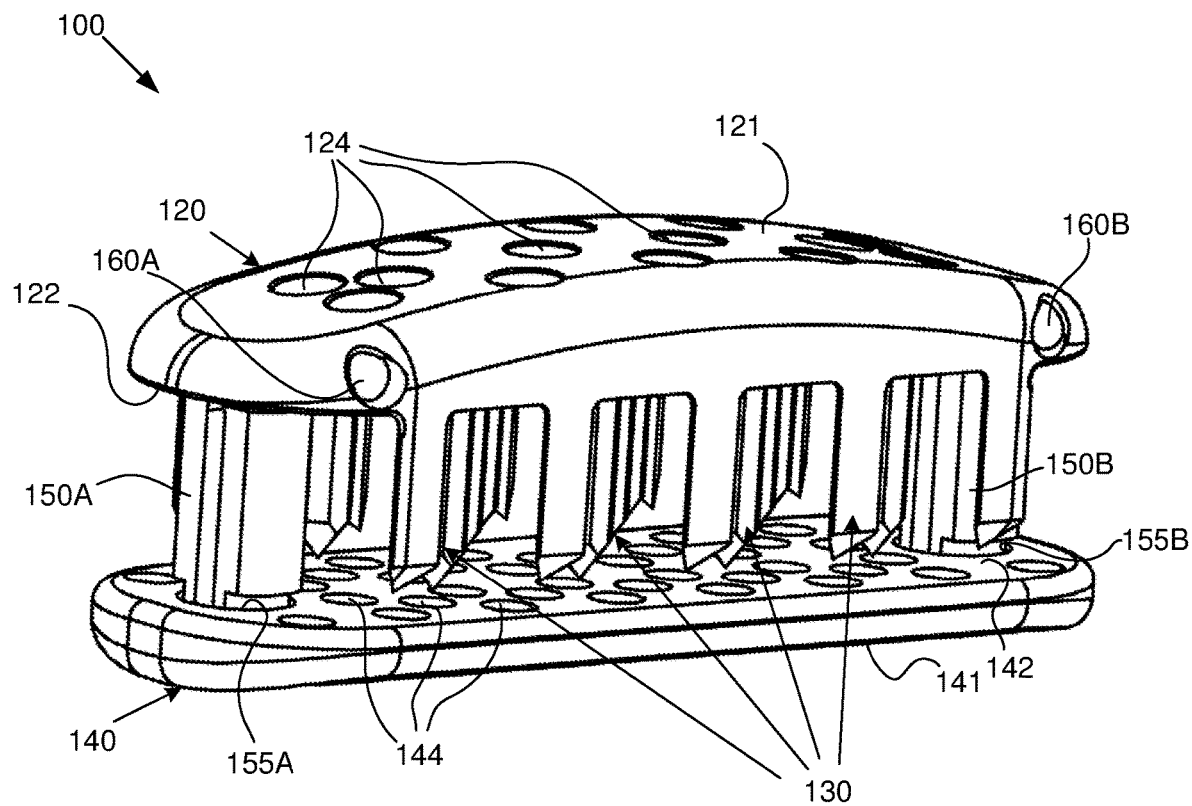
FIG. 1A is a front perspective view of a soft-tissue fixation device having a first plate, a second plate, and a plurality of tines, according to one embodiment.
Figure 1B:
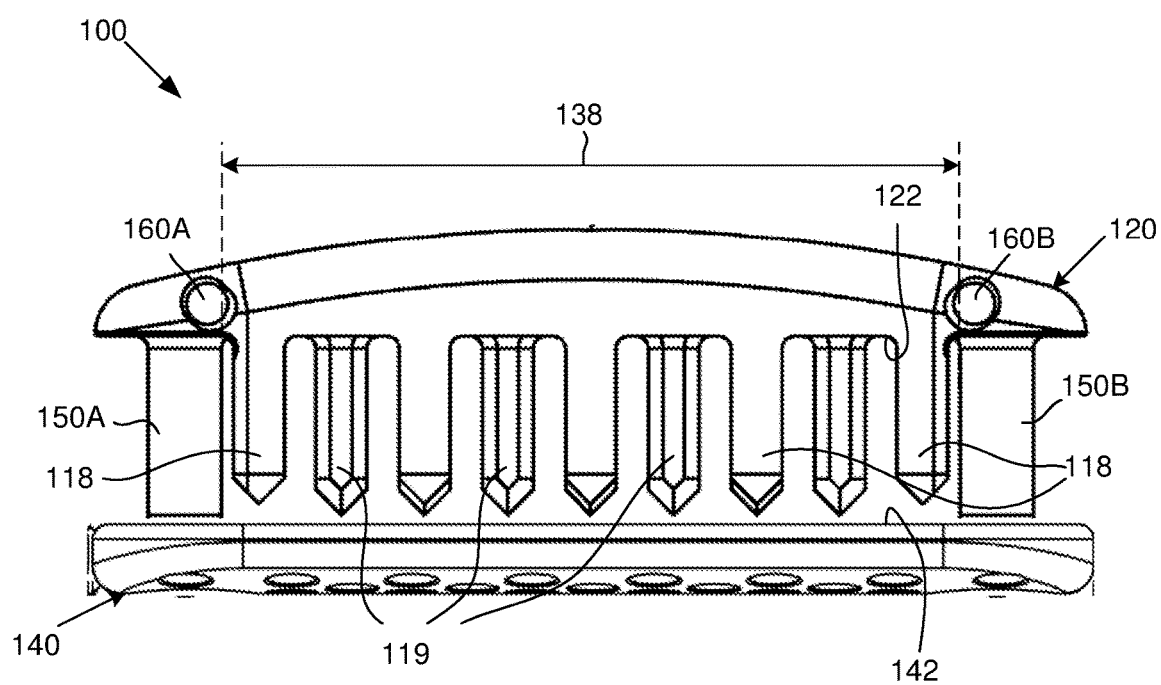
FIG. 1B is a front view of the soft-tissue fixation device of FIG. 1A, according to one embodiment.

FIGS. 1A and 1B show a front perspective view and a front view, respectively, of one embodiment of the soft-tissue fixation device 100. The soft-tissue fixation device 100 has a first plate 120, a second plate 140, and a plurality of tines 130. The first plate 120 has a first clamping surface 122 and the plurality of tines 130 extend from the first clamping surface 122. According to the embodiment depicted in the figures, the tines 130 are substantially parallel to each other. In another embodiment, the tines 130 may not be parallel to each other and may have different extension directions. For example, the tines 130 may have alternating extension directions. In another embodiment, tines may extend from both plates 120, 140.

The first plate 120 is configured to be positioned on a first side of a soft-tissue segment and the plurality of tines 130 extending from the first clamping surface 122 of the first plate 120 are configured to extend through the soft-tissue segment. The second plate 140 has a second clamping surface 142 and the second plate 140 is configured to be positioned on a second side of the soft-tissue segment with the second clamping surface 142 facing the first clamping surface 122. With the plates 120, 140 positioned on opposite sides of the soft-tissue segment, the tines 130 may be inserted and extend through the soft-tissue segment until the first plate 120 and the second plate 140 are connected together using a connection mechanism. The term "soft-tissue segment" refers to at least a partial portion or a partial section of a soft tissue. For example, in one embodiment, the plates 120, 140 are configured to clamp around the entire cross-sectional dimension of a soft tissue. However, in another embodiment, the plates 120, 140 clamp around only a partial cross-section of the soft tissue, thus one or both of the plates 120, 140 may actually be embedded within or disposed within the soft tissue. In other words, the use of the terms "first side" and "second side" of the soft-tissue segment may not necessarily refer to external sides of a soft tissue but instead may refer to internal surfaces/sides of the soft-tissue.

The soft-tissue fixation device 100 may be made from any of various materials, including metals, such as stainless steel and titanium, and synthetics, such as a rigid plastic, polymer, or composite. In another embodiment, the soft-tissue fixation device 100 is made from a bio-resorbable material. In an alternative embodiment, the soft-tissue fixation device is not implemented with the second plate, but instead the plurality of tines extending from the first plate are made from a shape-memory alloy (e.g., Nitinol). The shape of shape-memory alloys are temperature dependent. Accordingly, the tines may be inserted to extend through the soft-tissue segment and thereafter when the temperature of the plurality of tines is raised or lowered to a predetermined temperature (e.g., body temperature), the plurality of tines may undergo torsional deformation. The torsionally deformed tines intertwine with the fibers of the soft-tissue segment to securely hold the soft-tissue fixation device in place (while still allowing blood to flow through the soft-tissue segment).

The soft-tissue fixation device 100 is configured to securely attach to the soft-tissue segment while still allowing blood to flow through the soft-tissue segment. In one example, the soft-tissue fixation device 100 may be used to couple together two sections of a torn tendon. In another embodiment, to secure the soft tissue to bone, the soft-tissue fixation device 100 may be used as an anchor point to which cables or other surgically installed implements (pins, screws, etc) may be coupled. For example, the soft-tissue fixation device 100 may be used to secure soft-tissue to bone. According to the embodiment shown in the figures, the plates 120, 140 also include one or more pass-through apertures 124 and one or more cable holes 160A, 160B. The pass-through apertures 124, according to one embodiment, extend through the plates 120, 140 to promote proper blood flow through the soft-tissue segment being clamped by the soft-tissue fixation device 100.

Figure 2A:
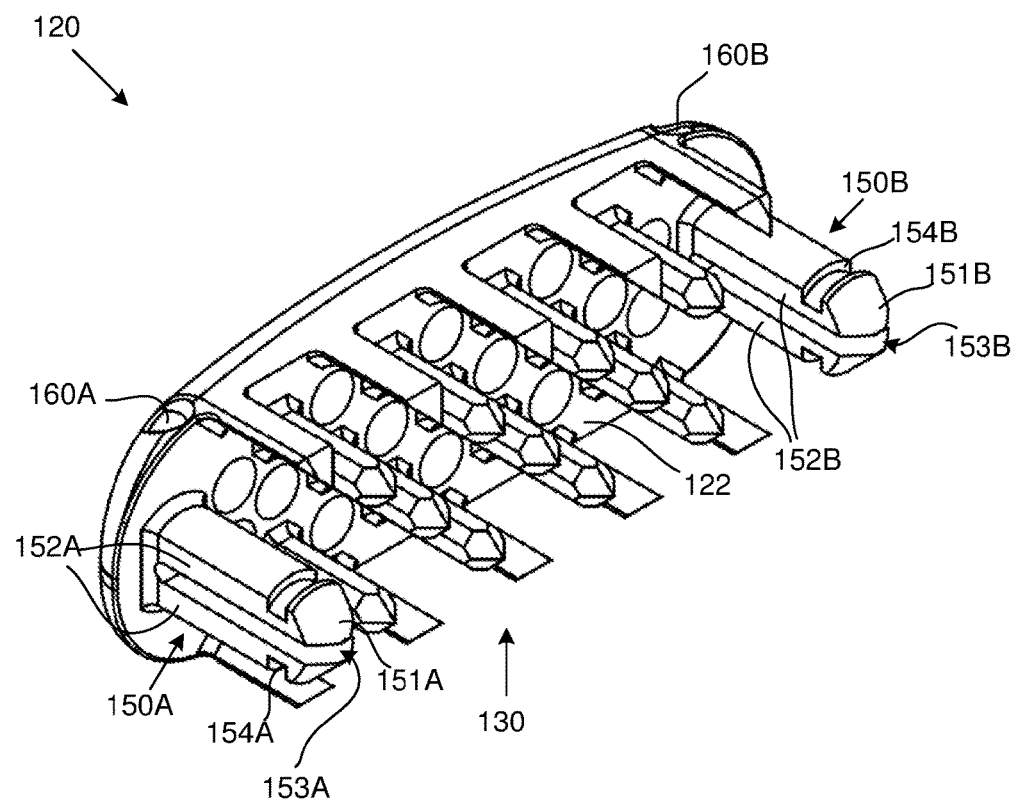
FIG. 2A is a bottom perspective view of the first plate of the soft-tissue fixation device, according to one embodiment.
Figure 2B:
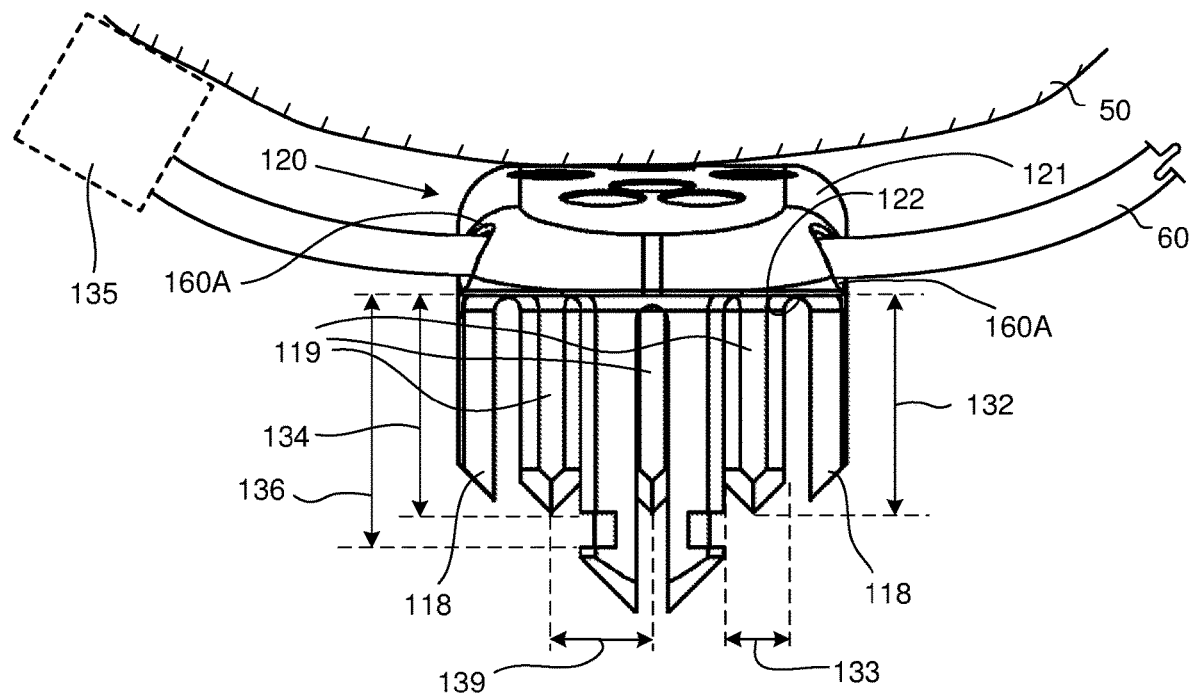
FIG. 2B is a side view of the first plate of the soft-tissue fixation device, according to one embodiment.

Referring to FIG. 2B, the soft-tissue fixation device 100 can be coupled with at least one other object using one or more tensionable cables 60. Generally, the soft-tissue fixation device 100 is coupled with another object to fixate the soft-tissue fixation device 100, and thus soft-tissue fixated by the soft-tissue fixation device, relative to that object. The at least one object can be one or more of any of various objects, such as the bone 50 and/or the object 135. The soft-tissue fixation device 100 and the at least one other object 135 are coupled together by coupling at least one cable 60 with both the soft-tissue fixation device and the at least one other object. Then, the soft-tissue fixation device 100 is fixated relative to the at least one other object 135 by tensioning the at least one cable 60 to a measurable and adjustable tension. The soft-tissue fixation device 100 may include at least one cable-retention feature to facilitate the coupling of the cable 60 to the soft-tissue fixation device 100.

In some implementations, one or more portions of the soft-tissue may be attached to a bone segment that has fractured or separated away from a bone. Accordingly, the bone segment can be rejoined with, or stabilized relative to, the bone by forming concentric holes through the bone segment and bone, passing a cable, such as cable 60, through the hole, and tensioning the cable to compress the bone segment and bone together with a measurable and adjustable compression. In some implementations, the same cable 60 used to fixate the soft-tissue fixation device 100 can be used to compress the bone segment and bone together.

According to yet certain implementations, tensioning the at least one cable 60 to a measurable and adjustable tension to fixate the soft-tissue fixation device 100 may also cause the soft tissue, fixated by the soft-tissue fixation device 100, to compress against bone, or alternatively compress against other soft tissue, with a measurable and adjustable compression.

The object 135 can be any of various objects, such as bone-anchoring objects, soft-tissue fixation devices, or other medical devices. For example, in one implementation, the object 135 is a bone-anchoring object (e.g., a bone anchor, bone pin, washer, external bone fixation device, internal bone fixation device, etc.) attached or fixed relative to the bone 50 such that directly coupling or fixating the soft-tissue fixation device 100 to the object 135 via the cable 60 indirectly couples or fixates the soft-tissue fixation device to the bone 50. As another example, in one implementation, the object 135 is a soft-tissue fixation device (secured or unsecured relative to bone) such that directly coupling or fixating the cable 60 to the soft-tissue fixation devices directly couples or fixates together the soft-tissue fixation devices.

In some implementations, the cable-retention features of the soft-tissue fixation device 100 are one or more cable holes 160A, 160B. The cables 60 are coupled to the soft-tissue fixation device 100 by passing the cables 60 through one or more of the cable holes 160A, 160B in the fixation device 100 as shown in FIG. 2B. In one embodiment, the cable holes 160A, 160B extend through the plates 120, 140 in a direction that is perpendicular to the extension direction of the tines 130. In another embodiment, the cable holes 160A, 160B may extend through the plates 120, 140 in a direction that is parallel with the extension direction of the tines 130. In yet another embodiment, the extension direction of the cable holes through the plates may be oblique relative to the extension direction of the tines. The cable-retention feature may be a recess or cavity that receives an end of the cables to facilitate pre-attachment of the cables 60 to the soft-tissue fixation device 100, such as by being fastened to, adhered to, boned to, embedded in, or crimped by, the soft-tissue fixation device. As mentioned above, after passing through one of the cable holes 160A, 160B of the soft-tissue fixation device 100, or after being pre-attached to the soft-tissue fixation device, a cable 60 may pass-through a hole or tunnel in a bone, or wrap around one or more tissues or bones (e.g., a cerclage configuration), before being tensioned.

According to one embodiment, the term "cable" refers to a cord-like element, such as a wire, filament, weave, or thread, whether bundled or individual, that is capable of holding a measurable and adjustable tension and causing a measurable and adjustable compression of bone, soft tissue, or both. In other words, the tension in the cable can be measured, such as by a tension measuring device, and can be adjusted, such as after an initial tensioning of the cable. When used to compress bone (e.g., to compress two bone segments together), soft tissue (e.g., to compress soft tissue segments together), or both, the measured tension in the cable is equal to a measured compression of the bone, soft tissue, or both. Thus, as used herein, a measured and adjustable tension of a cable is synonymous with a measured and adjustable compression of bone, soft tissue, or both by the cable.

In one embodiment, the measurable and adjustable tension may be a specific, known, predictable, expected, controllable, anticipated, desired, repeatable, sustainable, and/or predeterminable tension. For example, the cable may be passed through a pass-through hole in a bone and may be tensioned to a measurable and adjustable tension in order to facilitate the reduction and fixation of fractures or to otherwise facilitate the repair of dislocations or soft-tissue damage. In other words, the cable is not a conventional suture or conventional thread material, since such materials are incapable of, or at least not well-suited for, maintaining a measurable and adjustable tension. Thus, the term "cable" refers to a flexible yet substantially non-stretchable element that can be tensioned to a measurable and adjustable tension. In such an embodiment, because the cable is capable of maintaining or retaining a measurable and adjustable tension, the effectiveness and reproducibility of successful surgical procedures is improved. In other words, different surgical procedures relating to different bones in the body may involve different degrees of retention/fixation force (e.g., the fixation force required to reduce a fracture in the femur may be greater than the fixation force required to reduce a fracture in the patella). Accordingly, the ability of the cable to be tensioned to a measurable and adjustable tension improves the reliability and reproducibility of surgical procedures when compared with other medical procedures that do not utilize cables. The cable 60 may be made from any one of various materials. For example, in specific implementations, the cable 60 is made from metal, such as stainless steel, titanium, or other metal. As mentioned above, the tensioned cables can extend through the cable holes 160A, 160B in the soft-tissue fixation device 100 to secure or reattach the soft-tissue to bone.

As shown in FIGS. 1A-3B, the first plate 120 and the second plate 140 each has an external surface 121, 141 that is opposite the respective clamping surface 122, 142. According to one embodiment, the clamping surfaces 122, 142 are planar while the external surfaces 121, 141 of the plates 120, 140 are curved. In the depicted embodiment, the external surfaces 121, 141 also have curved edges and smooth corners. The curved and smooth nature of the external surfaces 121, 141 may conform to the shape of the tissues and body parts surrounding the soft-tissue segment.

Various types of connection mechanisms may be implemented to connect the two plates 120, 140 together to clamp around the soft-tissue segment with the tines 130 extending through the soft-tissue segment. In one embodiment, the connection mechanism not only connects the two plates 120, 140 together but also is configured as a spacing member to control the minimum distance between the clamping surfaces 122, 142 of the plates 120, 140. According to the embodiment depicted in the figures, the soft-tissue fixation device 100 includes two spacing members 150A, 150B extending from the first plate 120. These spacing members 150A, 150B are respectively engageable with two engagement features 155A, 155B of the second plate 140. In another embodiment, the spacing members may extend from the second plate and the engagement features may be disposed on the first plate.

The engagement between the spacing members 150A, 150B and the engagement features 155A, 155B maintains a predetermined distance between the first clamping surface 122 and the second clamping surface 142 that is equal to or more than a length 132 of the longest tine of the plurality of tines 130 (see, e.g., FIG. 2B). In one embodiment, the tines 130 may all have the same length. However, in another embodiment the tines 130 may have different lengths. Additional details relating to the dimensions and configuration of the tines 130 are included below with reference to the remaining figures. In one embodiment, the soft-tissue fixation device may have a single spacing member and its corresponding engagement feature. In another embodiment, the soft-tissue fixation device may have more than two spacing members. Additional details regarding the spacing members are included below with reference to FIG. 4.

Figure 3A:
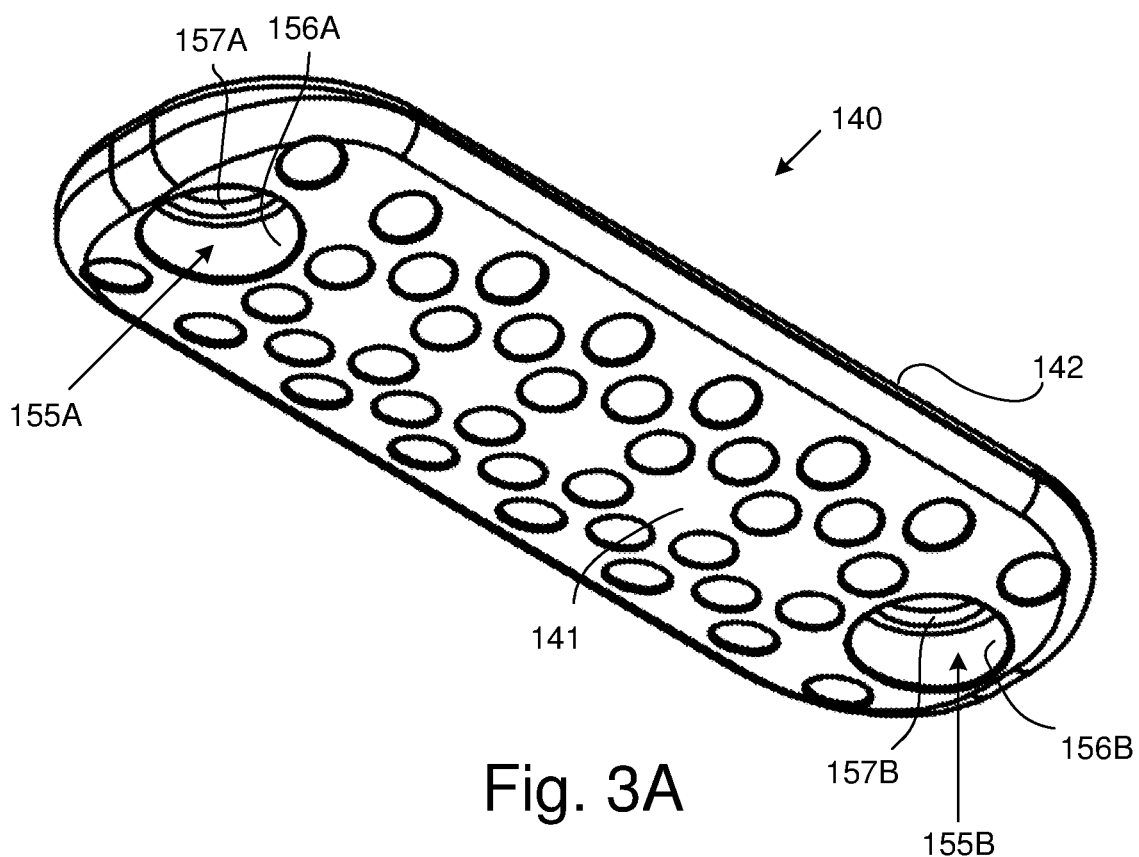
FIG. 3A is a bottom perspective view of the second plate of the soft-tissue fixation device, according to one embodiment.
Figure 3B:
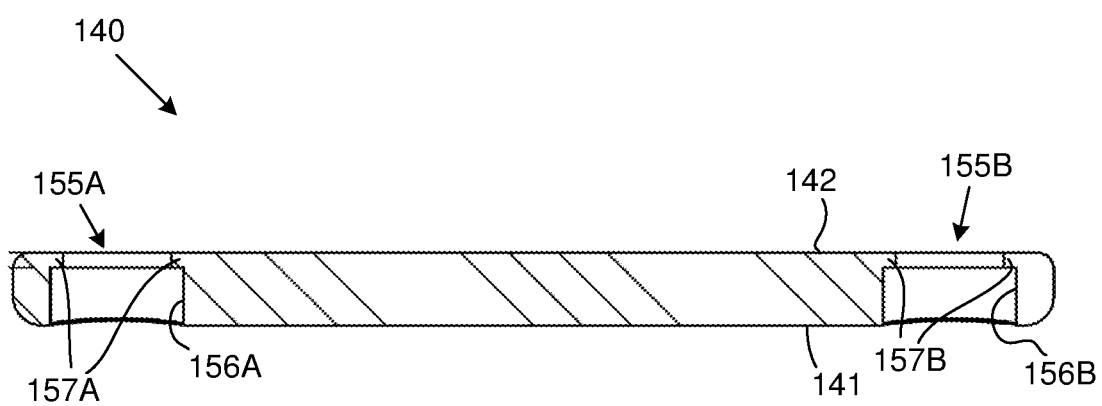
FIG. 3B is a front view of the second plate of the soft-tissue fixation device, according to one embodiment.

FIGS. 2A and 2B are a perspective view and a side view, respectively, of the first plate 120 of the soft-tissue fixation device 100. According to the depicted embodiment, at least a portion of each of the spacing members 150A, 150B is structured to have two prongs 152A, 152B made from a resiliently flexible material (in another embodiment, the spacing members may have more than two prongs). A gap 153A, 153B is interposed between the two prongs 152A, 152B such that the prongs 152A, 152B are bendable inwards toward each other. Each prong 152A, 152B has a tip 151A, 151B that converges towards the gap 153A, 153B in a direction from the first clamping surface 122 to the second clamping surface 142. Also, at least one of the prongs 152A, 152B of each spacing member 150A, 150B has a notch 154A, 154B on a lateral side. According to the depicted embodiment, the engagement features 155A, 155B are holes 156A, 156B and each hole has a lip 157A, 157B (FIGS. 3A and 3B). The two prongs 152A, 152B are configured to bend inwards as the tip 151A, 151B of each prong 152A, 152B of each spacing member 150A, 150B engages the lip 157A, 157B of the hole 156A, 156B upon insertion of the spacing member 150A, 150B into the hole 156A, 156B until the lip 157A, 157B is receivably engaged in the notch 154A, 154B.

According to the embodiments depicted in FIGS. 1A, 1B, 2A, and 2B, the notch 154A, 154B of each spacing member 150A, 150B has a width, as measured in a direction extending between the two plates 120, 140, that enables a degree of fluctuation in the distance between the first and second clamping surfaces 122, 142. For example, the lips 157A, 157B of the engagement features 155A, 155B may be able to move in the direction extending between the two plates while remaining locked within the notches 154A, 154B of the spacing members 150A, 150B. In such an example, the distance between the two plates 120, 140 may be allowed to fluctuate between a minimum distance 134 and a maximum distance 136. As mentioned above, the soft-tissue fixation device 100 holds securely to the soft-tissue segment while still allowing blood to flow through the soft-tissue segment clamped between the soft-tissue fixation device 100. Accordingly, the slight fluctuation in the distance between the two plates 120, 140 may facilitate adequate blood flow through the fixation device 100.

In one embodiment, the tines 130 are organized into one or more arrays of tines. As used herein, the term "array" refers to a section of tines 130 that has a uniform extension direction, a common location relative to the plates 120, 140, a common shape, etc. In one embodiment, all of the tines 130 form an array that is interposed between two spacing members 150A, 150B. In such an embodiment, the width of the array of tines may correspond with the width of the soft-tissue segment. In other words, a specific soft-tissue fixation device may be selected based on the width of its array of tines and the width of the specific soft-tissue segment to which the fixation device 100 will be coupled. In one embodiment, the soft-tissue segment has a width that allows it to fit between the two spacing members 150A, 150B, (i.e., the spacing members 150A, 150B are positioned and extend from proximate opposing edges of the first clamping surface 122) thus allowing the tines to intersect and extend through the soft-tissue segment while the spacing members 150A, 150B do not extend through the soft-tissue segment but instead form borders around the soft-tissue segment, thus improving the stability of the attachment of the soft-tissue fixation device 100 to the soft-tissue segment. However, in another embodiment, the spacing members 150A, 150B may be configured to intersect and extend through the soft-tissue segment.

In one embodiment, the tines are organized into an array that has rows of tines. The distance 139 between adjacent tines and/or adjacent rows of tines may be selected based on the specific type of soft-tissue segment. In one embodiment, the spacing between tines 130 has a significant effect on the amount of blood that is able to flow through the soft-tissue segment and also a significant effect on the stability of the attachment between the fixation device 100 and the soft-tissue segment. If the tines 130 are spaced too far apart from each other, the fixation device 100 will not be securely attached to the soft-tissue segment. Conversely, if the tines 130 are spaced too close to each other, the fixation device 100 will restrict blood flow through the soft-tissue segment, thus adversely affecting the natural healing process. In one embodiment, the distance 139 between rows of tines 130 is about 0.075 inches. The cross-sectional dimension 133 of each tine also has an effect on the blood flow of the soft-tissue segment and the stability of the fixation device 100.

In one embodiment, the plurality of tines 130 extends substantially perpendicularly from the first clamping surface 122. In one embodiment, each of the tines 130 has a non-circular cross-section (e.g., rectangular, polygonal, ovular, obround, etc). In another embodiment, the cross-section of the tines may be circular. According to the embodiment depicted in the figures, the tines also have a pointed tip that facilitates insertion of the tines through the soft-tissue segment. In another embodiment, as depicted in FIG. 2B, the plurality of tines 130 has peripheral tines 118 and middle tines 119. The peripheral tines 118 are the tines extending from proximate the edge of the first clamping surface 122 and the middle tines 119 are centrally located relative to the peripheral tines 118. In one embodiment, the peripheral tines 118 have tips of a first configuration (e.g., single surfaced) and the middle tines 119 have tips of a second configuration (e.g., multi-surfaced), the first configuration being different than the second configuration. In another embodiment, the length of the peripheral tines is different than the length of the middle tines (FIG. 1B). In yet another embodiment, the tines may be inclined relative to the clamping surface 122 (e.g., the tines may be oblique to the clamping surface 122).

Figure 4:
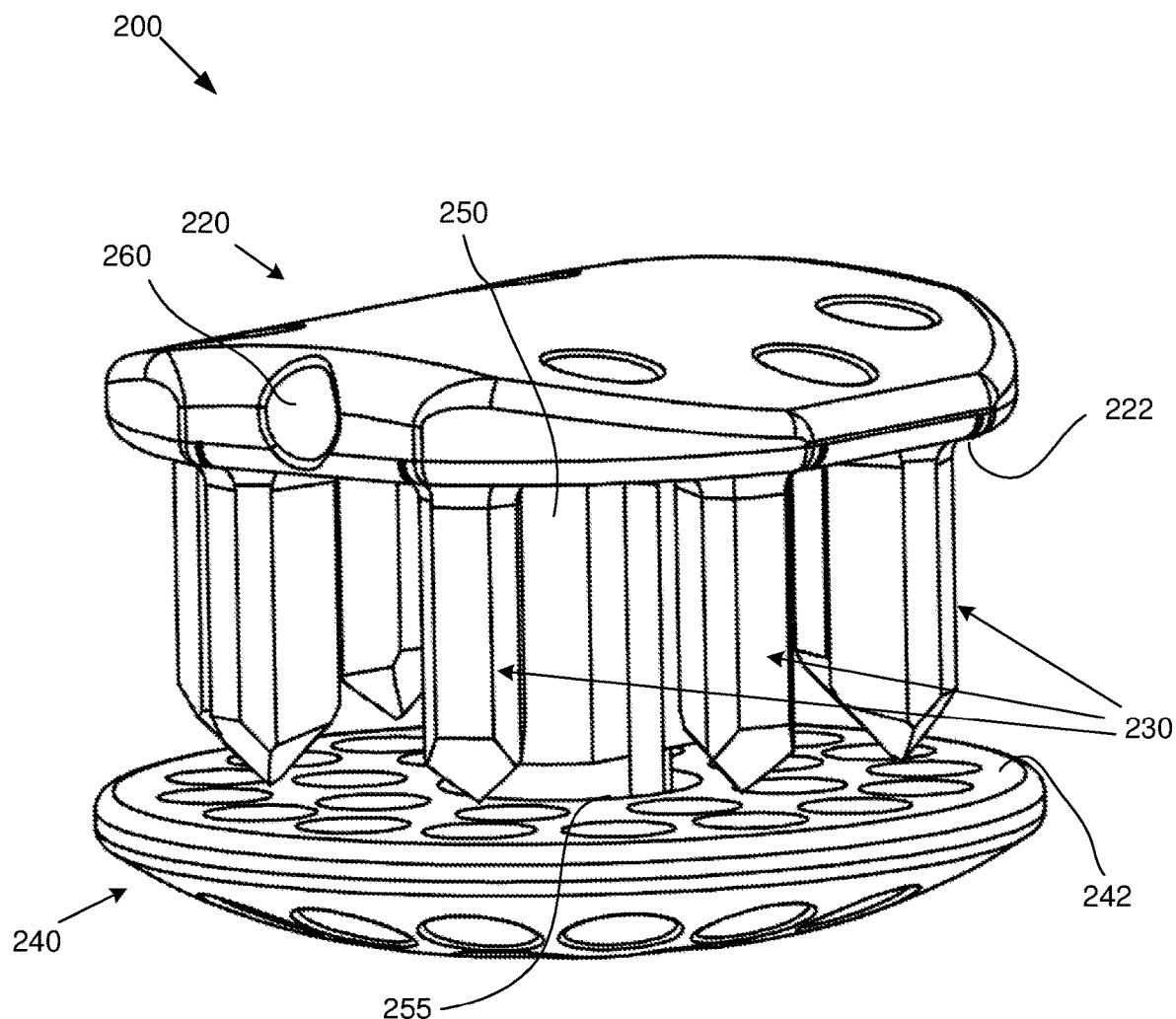
FIG. 4 is a front perspective view of another embodiment of the soft-tissue fixation device.

FIG. 4 is a front perspective view of another embodiment of the soft-tissue fixation device 200. In the depicted embodiment, the soft-tissue fixation device 200 has a single spacing member 250 that extends from a central location of the clamping surface 222 of the first plate 220. The central spacing member 250 engages the single central engagement feature 255 disposed on a central location of the second plate 240. The plurality of tines 230 are arranged around the central spacing member 250. The soft-tissue fixation device 200 depicted in FIG. 4 also shows a single cable hole 260 extending through the first plate 220 in a direction that is perpendicular to the extension direction of the tines 230. In one embodiment, the plates 120, 140 have a circular shape. In another embodiment, the plates 120, 140 are ovular, elliptical, or obround (e.g., racetrack like).

Figure 5:
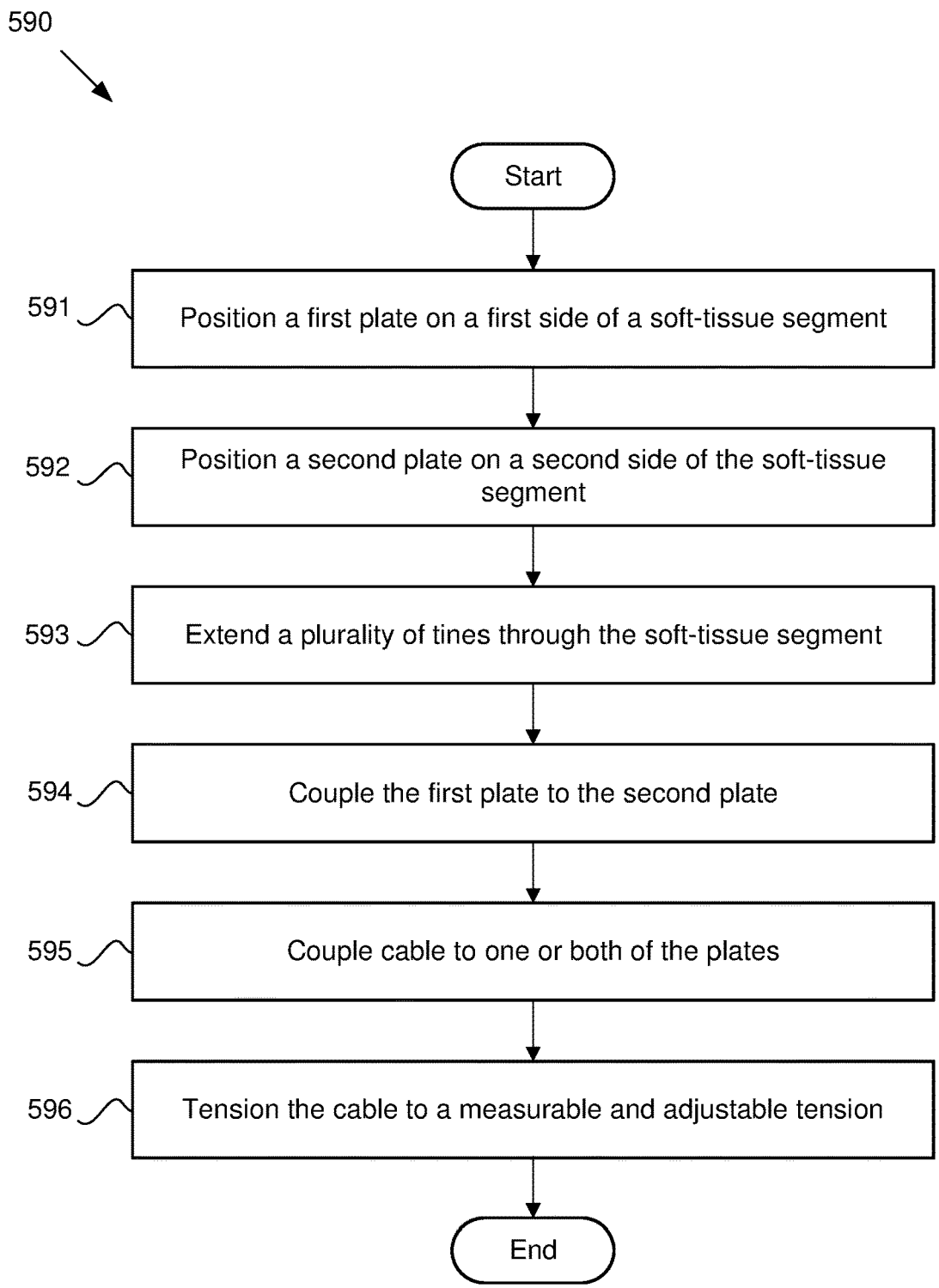
FIG. 5 is a schematic flowchart diagram of a method for repairing a damaged or torn soft-tissue, according to one embodiment.

FIG. 5 is a schematic flowchart diagram of a method 590 for stapling a soft-tissue segment. The method 590 includes positioning the first plate on the first side of the soft-tissue segment at 591 and positioning the second plate on the second side of the soft-tissue segment at 592. The method 590 further includes extending the plurality of tines through the soft-tissue segment at 593 and then subsequently coupling the first plate to the second plate by engaging at least one spacing member of one of the first plate and the second plate with at least one engagement feature of the other of the first plate and the second plate at 594. Engagement between the at least one spacing member and the at least one engagement feature maintains a predetermined distance between the first clamping surface and the second clamping surface that is more than a length of any one of the tines.

In one embodiment, the soft-tissue segment is a first soft-tissue segment and positioning the first plate on the first side of the first soft-tissue segment includes positioning the first plate on a first side of a second soft-tissue segment. In such an embodiment, positioning the second plate on the second side of the first soft-tissue segment includes positioning the second plate on a second side of the second soft-tissue segment. Accordingly, extending the plurality of tines through the first soft-tissue segment includes extending a first grouping of the plurality of tines through only the first soft-tissue segment, extending a second grouping of the plurality of tines through only the second soft-tissue segment, and extending a third grouping of the plurality of tines through both the first and second soft-tissue segments to couple the first and second soft-tissue segments together. In other words, the first and second soft-tissues segments are partially overlapped before being secured together. The method 590 further includes coupling a cable to one or both of the first or second plates, which may include extending a cable through a cable-hole in one of the first or second plates, at 595 and tensioning the cable to a measurable and adjustable tension to fixate the soft-tissue fixation device relative to an object at 596, to cause, in some implementations, a measurable and adjustable compression of the soft tissue against bone and/or compression of the soft tissue against another soft tissue segment. In one embodiment, the method 590 may optionally include releasing and re-tensioning the cable to the same or a different measurable and adjustable tension.

Figure 6:
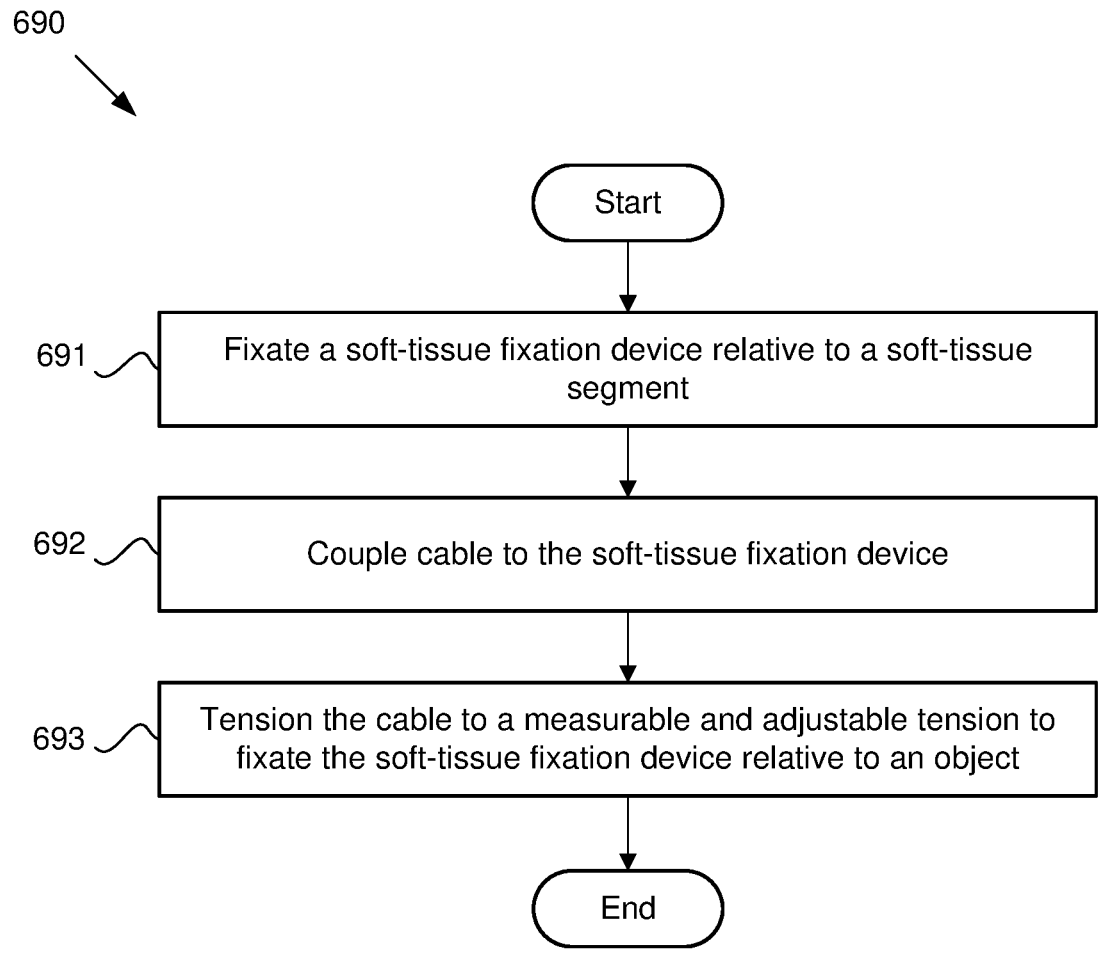
FIG. 6 is a schematic flow chart diagram of one embodiment of a method for fixating soft-tissue relative to bone.

FIG. 6 is a schematic flow chart diagram of one embodiment of a method 690 for fixating soft-tissue relative to bone. The method 690 includes fixating a soft-tissue fixation device relative to a soft-tissue segment at 691, coupling a cable to the soft-tissue fixation device at 692, and tensioning the cable to a measurable and adjustable tension to fixate the soft-tissue fixation device relative to an object at 693, to cause, in some implementations, a measurable and adjustable compression of the soft tissue against bone and/or compression of the soft tissue against another soft tissue segment.

As described above with reference to method 590, method 690 may optionally include, after the cable is tensioned to a measurable and adjustable tension, releasing the tension in the cable and re-tensioning the cable to the same or different measurable and adjustable tension. Releasing the tension in the cable may include unlocking a lock that is configured to maintain the cable in tension. The ability to release tension in a cable and subsequently re-tension the cable provides various advantages, such as, for example, facilitating re-use of the cable on other targeted areas of the body in one or more subsequent procedures, in some implementations, and adjustment to the tension or position of the cable on the same targeted area of the body in the same or a subsequent procedure, in other implementations.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C; or some other suitable combination. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The subject matter of the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A soft-tissue fixation device, comprising:
    a first plate comprising a first clamping surface and a plurality of tines extending from the first clamping surface, wherein the first plate is configured to be positioned on a first side of a soft-tissue segment and the plurality of tines are configured to extend through the soft-tissue segment; and
    a second plate comprising a second clamping surface, the second plate configured to be positioned on a second side of the soft-tissue segment and the second clamping surface configured to face the first clamping surface of the first plate;
    wherein one of the first plate and the second plate comprises at least one spacing member and the other of the first plate and the second plate comprises at least one engagement feature configured to engage the at least one spacing member; and
    wherein engagement between the at least one spacing member and the at least one engagement feature maintains a predetermined distance between the first clamping surface and the second clamping surface that is more than a length of any one of the tines.

2. The soft-tissue fixation device of claim 1, wherein the plurality of tines extend substantially perpendicularly from the first clamping surface.

3. The soft-tissue fixation device of claim 1, wherein the plurality of tines are substantially parallel to each other.

4. The soft-tissue fixation device of claim 1, wherein the first plate comprises at least one cable hole configured to receive a tensionable cable therethrough.

5. The soft-tissue fixation device of claim 1, wherein the plurality of tines comprises peripheral tines and middle tines, the peripheral tines having tips of a first configuration and the middle tines having tips of a second configuration, the first configuration being different than the second configuration.

6. The soft-tissue fixation device of claim 1, wherein spacing between adjacent tines of the plurality of tines and the predetermined distance between the first clamping surface and the second clamping surface enable the soft-tissue fixation device to be securely attached to the soft-tissue segment while still allowing blood to circulate through the soft-tissue segment.

7. The soft-tissue fixation device of claim 1, wherein the plurality of tines each has a non-circular cross-section.

8. The soft-tissue fixation device of claim 1, wherein the plurality of tines have the same length.

9. The soft-tissue fixation device of claim 1, wherein:
    the at least one spacing member comprises two prongs made from a resiliently flexible material;
    a gap is interposed between the two prongs such that the prongs are bendable inwards toward each other;
    each prong has a tip converging towards the gap in a direction from the first clamping surface to the second clamping surface and each prong has a notch on a lateral side;
    the at least one engagement feature comprises a hole having a lip; and
    the two prongs are configured to bend inwards as the tip of each prong engages the lip of the hole upon insertion of the at least one spacing member into the hole until the lip is receivably engaged in the notch.

10. The soft-tissue fixation device of claim 1, wherein:
    the plurality of tines form an array of tines;
    the at least one spacing member comprises two spacing members;
    the at least one engagement feature comprises two engagement features; and
    the array of tines is interposed between the two spacing members and the two engagement features.

11. The soft-tissue fixation device of claim 10, wherein the array of tines has a width, the width being less than a distance between the two spacing members.

12. The soft-tissue fixation device of claim 1, wherein the first clamping surface is planar, the first plate comprising an outer surface opposing the first clamping surface, wherein the outer surface is substantially contoured.

13. The soft-tissue fixation device of claim 1, wherein the plurality of tines form an array of tines, and wherein the array of tines comprises rows of tines, wherein a distance between adjacent rows is about 0.075 inches.

* * * * *